United States Patent [19]
Hauptli et al.

[11] Patent Number: 5,599,276
[45] Date of Patent: Feb. 4, 1997

[54] DIOPTER VALUE VIEWING MEANS FOR A VIDEO OPHTHALMOSCOPE

[75] Inventors: Ronald Hauptli, Warners; Andrew J. Kugler, Jamesville, both of N.Y.

[73] Assignee: Welch Allyn, Inc., Skaneateles Falls, N.Y.

[21] Appl. No.: 600,504

[22] Filed: Feb. 13, 1996

[51] Int. Cl.$^6$ ........................................................ A61B 3/13
[52] U.S. Cl. ........................... 600/112; 351/206; 351/218
[58] Field of Search ............................ 128/745; 600/103, 600/112, 117, 179, 188–189, 200, 249; 606/4, 10; 351/205, 206, 217–218

[56] References Cited

U.S. PATENT DOCUMENTS

| | | | |
|---|---|---|---|
| 3,035,483 | 5/1962 | Andreas et al. | 351/218 |
| 3,638,643 | 2/1972 | Hotchkiss | 600/200 |
| 3,832,042 | 8/1974 | Heine | 351/205 |
| 4,526,449 | 7/1985 | Newman et al. . | |
| 4,533,222 | 8/1985 | Ishikawa | 351/206 |
| 4,643,546 | 2/1987 | Richards . | |
| 4,998,818 | 3/1991 | Kugler et al. . | |
| 5,239,984 | 8/1993 | Cane et al. . | |
| 5,363,839 | 11/1994 | Lankford | 600/112 |
| 5,527,262 | 6/1996 | Monroe et al. | 600/110 |
| 5,528,323 | 6/1996 | Fujieda et al. | 351/218 |

*Primary Examiner*—Richard J. Apley
*Assistant Examiner*—David R. Risley
*Attorney, Agent, or Firm*—Harris Beach & Wilcox, LLP

[57] ABSTRACT

There is a hand-held opto-diagnostic medical system comprising a medical instrument including a housing having an optical passage through the housing and a light source for illuminating the target area. The medical instrument has a plurality of optical lenses with varying diopters fixed to one or more rotatably mounted lens selection discs which are mounted within the housing and positioned to lie in a plane perpendicular to the optical passage. The rotation of the discs sequentially disposes one or a combination of the lenses into the optical passage. The front face of the housing has a window with an indicator to display the diopter value of the lens or lenses disposed. The system further comprises an adapter coupled to the front face of the housing. The adapter has a beam splitter mechanically and optically coupled into the adapter. An optical input originates from the optical passage of the medical instrument and extends into the beam splitter, a first optical output of the beam splitter communicated to a system eyepiece positioned in the front face of the adapter, and a second optical output of the beam splitter communicated to a video camera head positioned within the adapter. By use of mirrored reflectors, such as a prism, located between the medical instrument and the adapter, the physician is able to view the diopter indicator window while the video adapter is coupled to the medical instrument.

5 Claims, 6 Drawing Sheets

DIOPTER VALUE VIEWING MEANS FOR A VIDEO OPHTHALMOSCOPE

Pursuant to 37 C.F.R. § 1.78(a)(3), this nonprovisional application claims benefit of the provisional application Ser. No. 06/004,110 dated Sep. 21, 1995.

BACKGROUND OF THE INVENTION

1. Field of the Invention

This invention relates generally to medical diagnostic instruments and more specifically to a hand-held opto-diagnostic instrument having an adaptor for connecting the medical instrument to a video camera.

2. Discussion of Related Art

Hand-held medical instruments for use by a physician in the optodiagnosis of patients have been kayown for some time. Such hand-held instruments include the otoscope and ophthalmoscope. The hand-held optodiagnostic medical instruments often include a plurality of lenses typically arrayed on one or more discs contained within the instrument head housing which can be manipulated by the physician to selectively dispose a lens or combination of lens, disclosed in more detail by U.S. Pat. No. 4,643,546 to Richards, U.S. Pat. No. 4,526,449 to Newman et al., and U.S. Pat. No. 4,998,818 to Kugler et al., which have been assigned to a common assignee together with the present application and are incorporated herein by reference. The physician selects a lens or combination of lenses for the desired optical properties appropriate for the inspection of a specific target area. The physician selects a lens or a combination of lenses to adjust for the target area being viewed, the patient's refractive error, and the physician's refractive error. The diopter of the specific lens or combination of lenses selected is indicated through a window in the housing of the medical instrument, as is known in the past.

It is also known in the art to employ video technology in combination with hand-held diagnostic medical instruments through the use of an adapter which is removably secured to the instrument, as disclosed by U.S. Pat. No. 5,239,984 granted Aug. 31, 1993 to Cane et al., which is incorporated herein by reference. The adapter utilizes a beam splitter which provides two optical outputs. One of the optical outputs goes to the medical system eyepiece to enable the physician to obtain a direct view of the target area, such as the retina of the eye. The second optical output goes to a video camera head, typically a solid state imager such as a charged coupled device. This allows for video output of the target area for use in producing hard copy photographs, real-time video display, or telecommunication links to remote video hook-ups.

One difficulty experienced in the use of such instruments is the inability of the physician to view the window in the housing of the medical instrument which indicates the diopter of the lens currently in use while the video adapter is employed. When the physician uses the instrument, the physician must view an object through the instrument and adjust the lens dial to obtain proper focus. While keeping the unit aimed at the same object, the physician views the image on the video monitor, and then adjusts the focus ring just above the video camera head until the image is in focus on the monitor.

It is useful to know the value of the diopter of the lens employed because different users may have different refractive errors. Also, a user may change between wearing eyeglasses or not wearing eyeglasses which would require a refocusing of the instrument. An easier view of the diopter value is thus advantageous because it allows the user to reduce the amount of time and effort needed to efficiently operate the instrument.

SUMMARY OF THE INVENTION

According to the present invention, there is a hand-held opto-diagnostic medical system comprising a medical instrument including a housing having an optical passage through the housing and a light source for illuminating the target area. The medical instrument has a plurality of optical lenses with varying diopters fixed to one or more rotatably mounted lens selection discs which are mounted within the housing and positioned to lie in a plane perpendicular to the optical passage. The rotation of the discs sequentially disposes one lens or a combination of the lenses into the optical passage. The front face of the housing has a window with an indicator to numerically display the diopter value of the lens or lenses disposed. The system further comprises an adapter coupled to the front face of the housing. The adapter has a beam splitter mechanically and optically coupled into the adapter. An optical input originates from the optical passage of the medical instrument and extends into the beam splitter, a first optical output of the beam splitter communicated to a system eyepiece positioned in the front face of the adapter, and a second optical output of the beam splitter communicated to a video camera head positioned within the adapter. By use of mirrored reflectors, or a prism, located between the medical instrument and the adapter, the physician is able to view the diopter indicator window while the video adapter is coupled to the medical instrument.

BRIEF DESCRIPTION OF THE DRAWING

For a fuller understanding of the nature and objects of the invention, reference should be made to the following detailed description of a preferred mode of practicing the invention, read in connection with the accompanying drawings, in which.

DETAILED DESCRIPTION OF THE INVENTION

Figure 1:
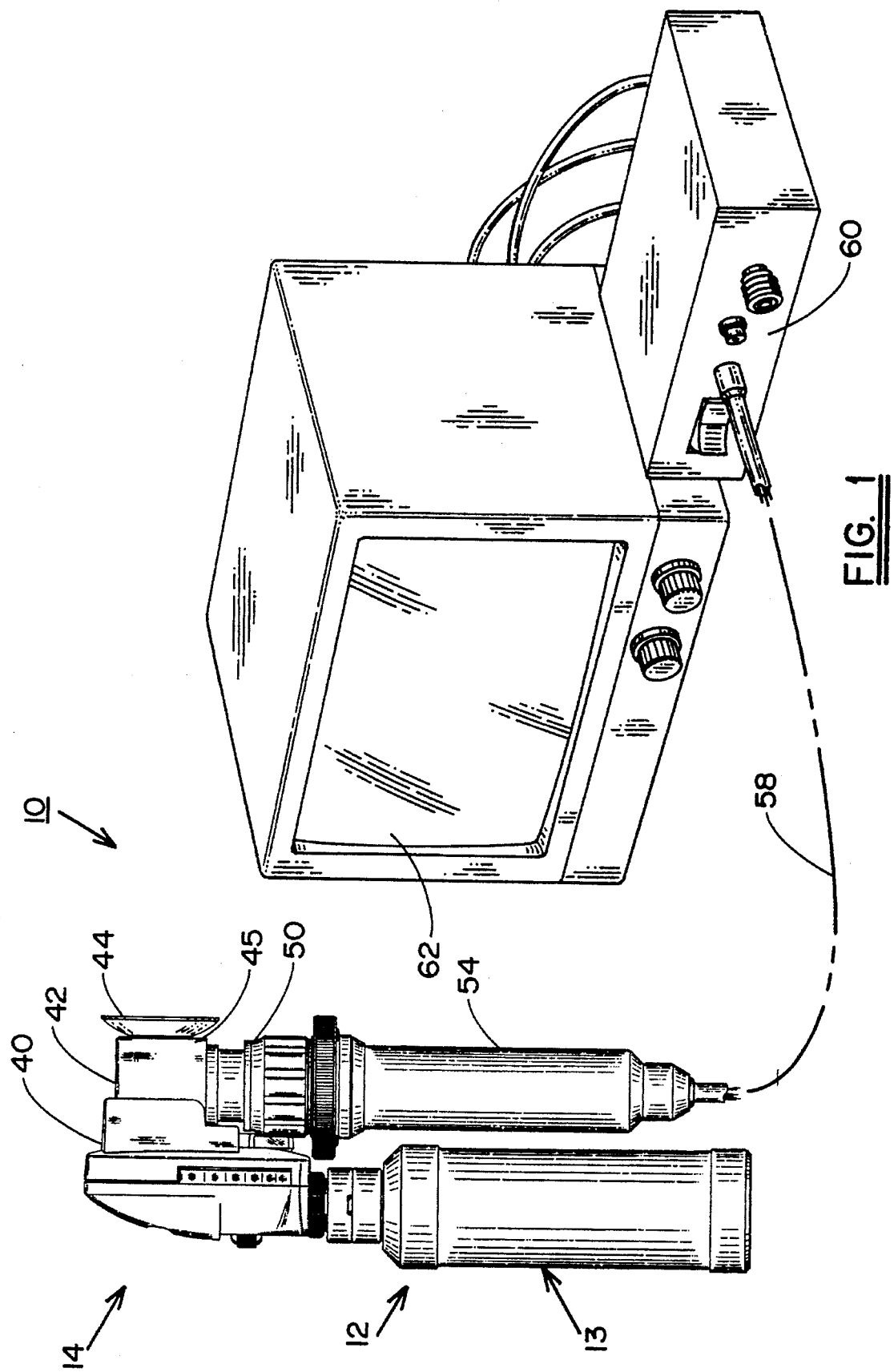
FIG. 1 is a perspective view of the opto-diagnostic medical system.

Referring now to FIG. 1, there is shown an opto-diagnostic medical system 10 as disclosed by U.S. Pat. No. 5,239,984 granted Aug. 31, 1993 to Cane et al. The system provides for the placement of a customized adaptor bracket or coupling 40 upon the existing instrument head 14 of the existing ophthalmoscope 12. The ophthalmoscope 12 has a handle 13, which in a preferred embodiment also serves as a battery storage. It is to be understood that the term ophthalmoscope as used hereinafter is used in a sense equivalently to the term otoscope in that, for purposes of the present invention, the function of these other hand-held diagnostic instruments is equivalent to that of the ophthalmoscope.

The adaptor 42 has a system eyepiece 44 on the front face 45 and an image coupler 50, which in a preferred embodiment comprises a remote video head (not shown) utilizing a charge coupled device, contained in the video housing 54 and connected to a processor 60 by an electronic cable 58 which in turn can be connected to a video monitor 62. It is also understood that the processor can feed video output inflation to devices that can produce hard copies or to communication ports, not herein illustrated.

Figures 2, 2A:
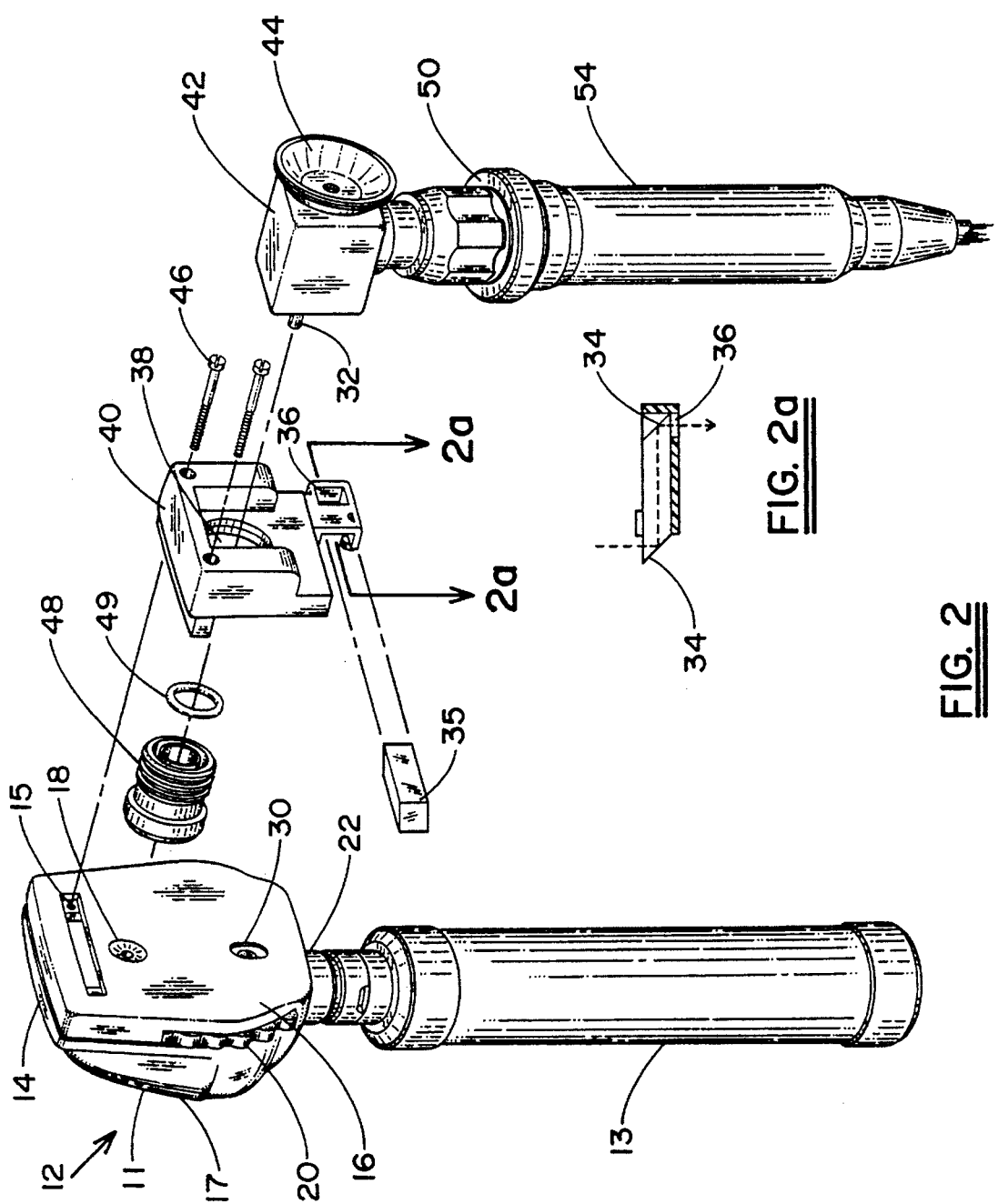
FIG. 2 is an exploded perspective view of the adaptor bracket, adaptor, and prism assembly.
FIG. 2a is a top view of the prism assembly.
Figure 3:
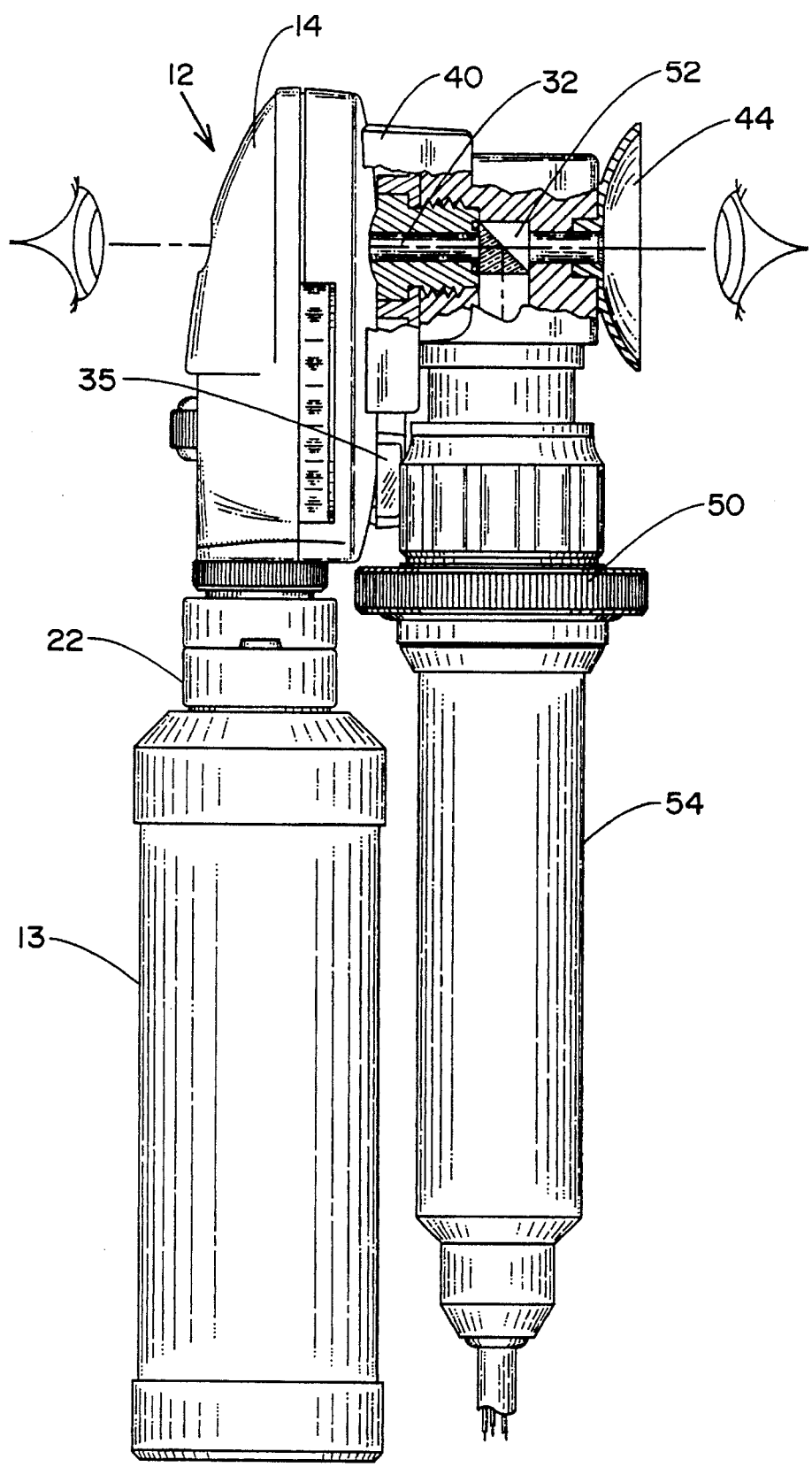
FIG. 3 is partial vertical sectional view of the adaptor bracket and adaptor assembly.
Figure 4:
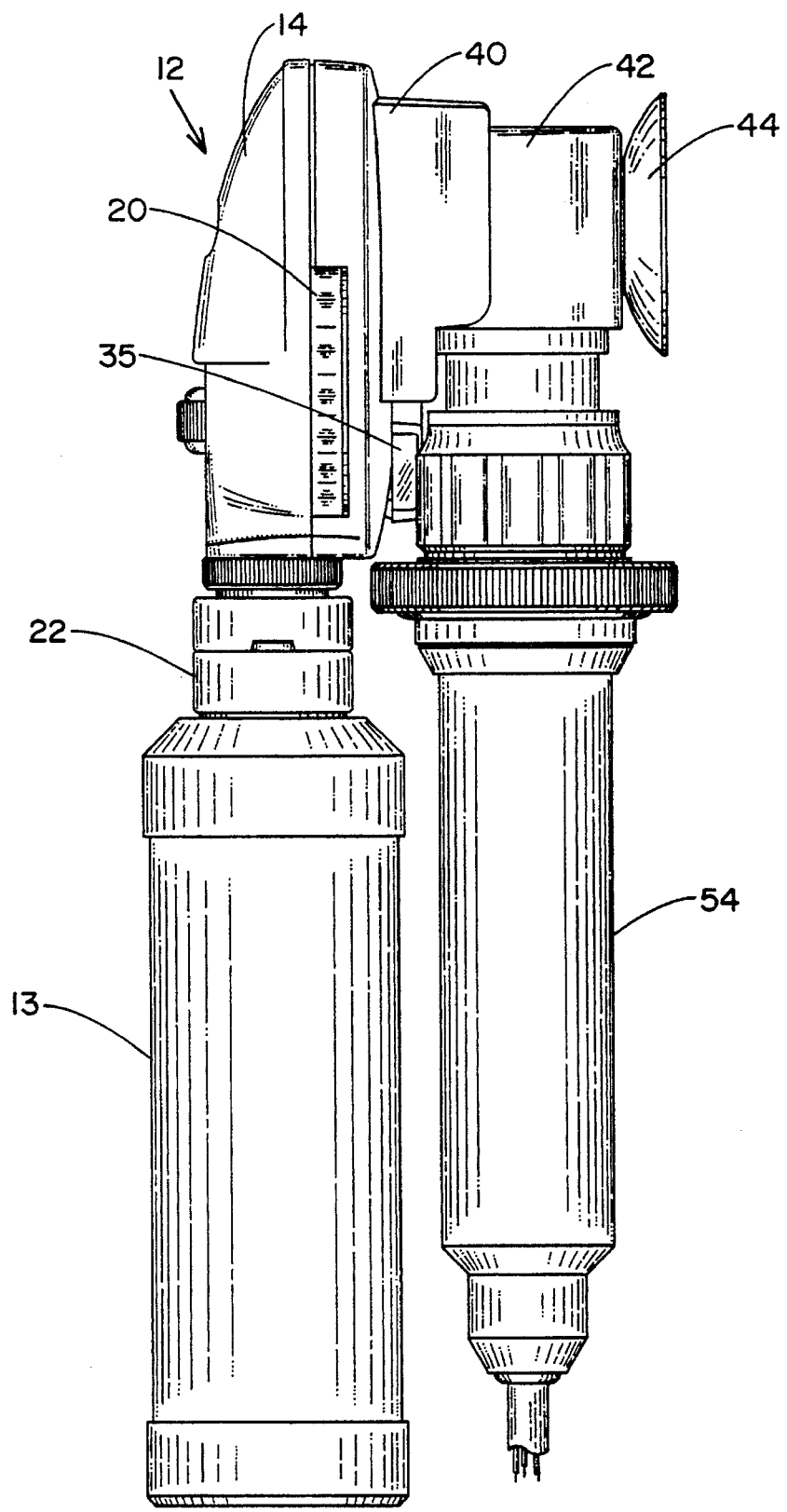
FIG. 4 is side elevational view of the ophthalmoscope and adapter while assembled.

Referring now to FIGS. 2–4, there is an ophthalmoscope 12 which has an instrument head 14 with a housing 11, the housing 11 having a front face 16, a rear face 17, and an optical passageway 18 passing therethrough. The instrument head 14 contains most of the elements of the optical system and has a neck 22 that is adapted to be releasably connected to a conventional battery handle 13. Provided in the neck 22 of the ophthalmoscope 12 is a light source, not shown. The light source preferably consists of a curved filament bulb (not shown) as disclosed in the above patent '449 that permits a virtual coaxial alignment of the illumination path and the viewing path to eliminate as many annoying shadows as possible.

Figure 5:
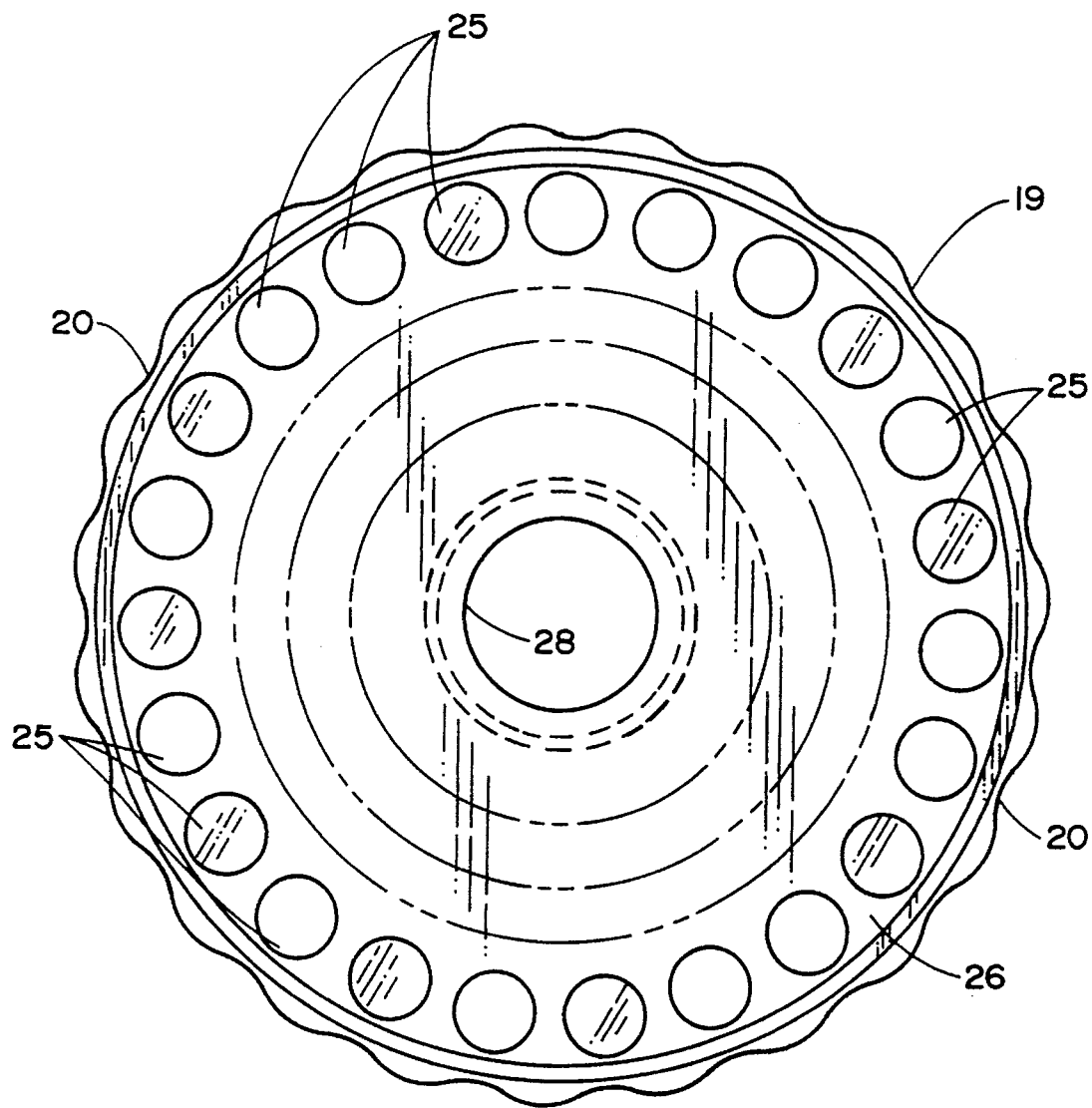
FIG. 5 is an elevational view of the lens disc.

Referring now to FIG. 5, contained within the housing 11 is a plurality of lenses 25 disposed on one or more rotatable discs 19. The lens disc 19 is an assembly comprised of a central, transparent disc element 26 and a scalloped rim 20 that is secured to the disc element as by ultrasonic welding. The disc element 26 has a plurality of circumferentially disposed lenses 25, the element 26 being preferably of plastic and the lenses 25 being molded therein with optical precision. Disc element 26 has a central opening 28 which receives and is rotatable on a hollow hub (not shown). The discs are rotated by the physician through the manipulation of the scalloped rim 20 of the disc, which extends outside of the housing 11. By manipulating the scalloped rim 20, the physician disposes a lens 25, or combination of lenses when the instrument utilizes more than one disc, into the optical passageway 18. In addition, the ophthalmoscope 12 may include other features such as varying linear polarizers, filters and apertures, as is known in the art.

Figure 6:
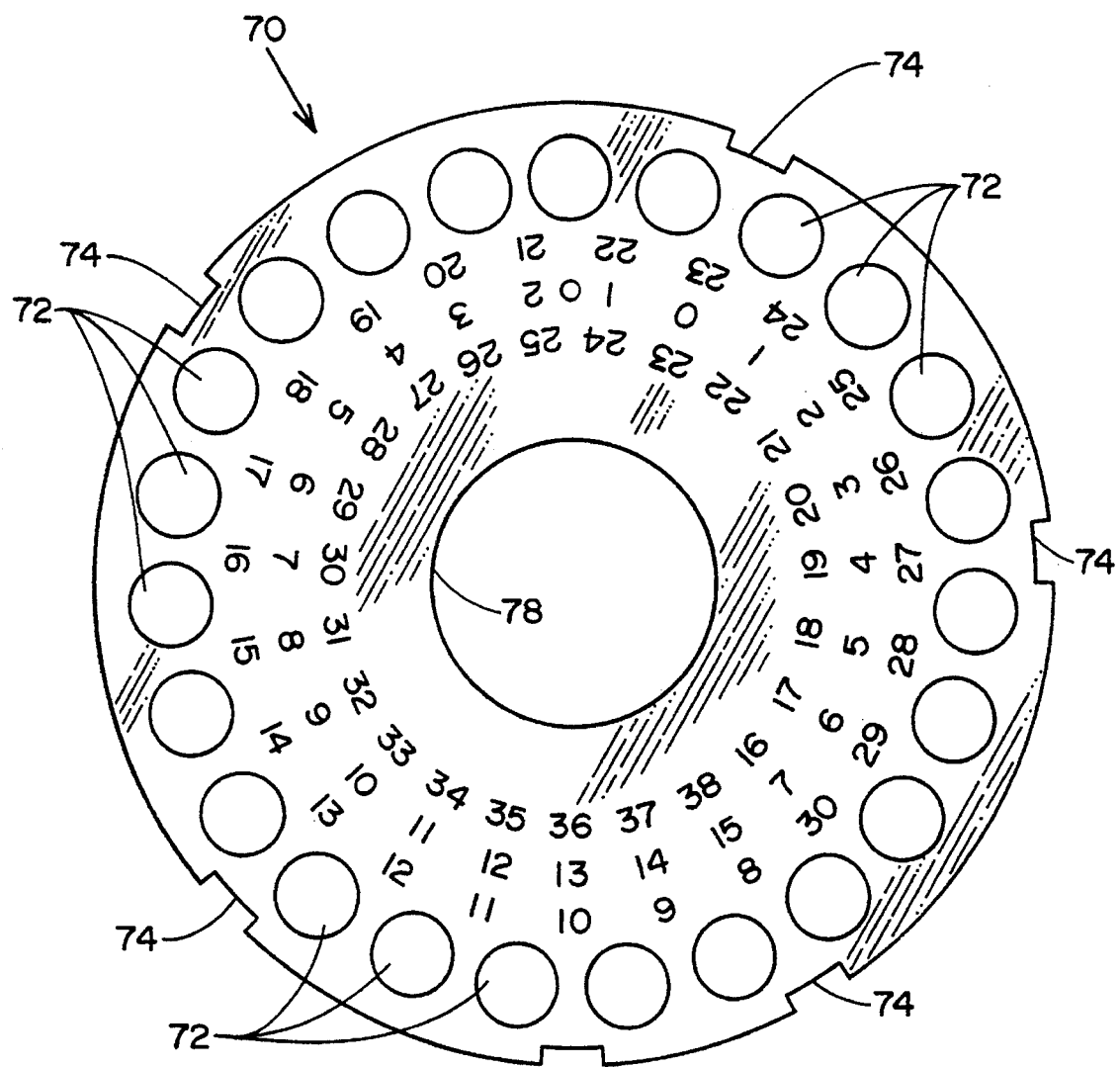
FIG. 6 is an elevational view of the film bearing the lens diopter numbers.

The housing 11 of the instrument head 14 further comprises a window 30 on the front face 16. The window 30 allows for viewing numbers which indicate the particular diopter value of the lens or lenses that have been selectively disposed in the optical passageway 18. These numbers appear on a disc shaped piece of film 70 (FIG. 6) that overlies the rear side of the lens disc 19, the film disc 70 having a central hole 78 in alignment with the central hole 28 of the lens disc 19 to accommodate the hub (not shown). Adjacent its periphery, the film disc 70 has circular holes 72 which register with the lenses 25 in the lens disc 19. To properly locate the film disc 70 relative to the underlying lens disc 19, the film disc 70 is provided with peripheral locator recesses 74 that mate with conforming lugs (not shown) on the lens disc 19. The film disc 70 is essentially opaque but the diopter numbers are clear or translucent so that light rays from the light source (not shown) will pass through them making the numbers visible through the window 30. As is conventional, the diopter numbers are diametrically opposite the lenses they represent.

The ophthalmoscope 12 is coupled to the video adaptor 42. The video adaptor 42 has a beam splitter 52 (FIG. 3) contained therein which is aligned with the optical passageway 18. The beam splitter 52 is an optical device which divides an incoming beam of light into two light outputs, typically through the use of an inclined plane having a partial refractive property such that a portion of the incoming beam of light will be refracted or diverted from its incident direction while an unrefracted portion of the incoming beam will continue along its original path of propagation to the system eyepiece 44. The portion of the beam that is retracted or diverted is directed to the video head 54.

The ophthalmoscope 12 is coupled to the video adaptor 42 by an adaptor coupling or bracket 40. The adaptor bracket 40 includes coupling means such as screws 46 or a threaded retainer 48 with an "O" ring 49, or combinations thereof. In addition, the instrument head 14 may contain apertures 15 that are designed to accept the screws 46 or threaded retainer 48 to provide a secure fit of the adaptor 42 to the ophthalmoscope 12. The adaptor bracket 40 includes an optical passageway 38 which, in the preferred embodiment, is shaped to accommodate a rod lens 32 affixed to the adaptor 42. The rod lens 32 serves to place the beam splitter 52 in optical communication with the optical passageway 18 of the ophthalmoscope 12.

When the ophthalmoscope 12 is coupled to the video adaptor 40 as depicted in FIG. 4, the window 30 in the front face 16 of the housing 11 which displays the diopter value is occluded by the image coupler 50. In order to allow the physician a view of the diopter value of the lens or lenses that have been selected, there is disposed between the image coupler 50 and the ophthalmoscope 12 means to reflect the diopter value indicated from the window 30 of the ophthalmoscope housing 11 to a position visible from the front side of the adaptor 42.

Referring now to FIG. 2a, the reflecting means depicted include a prism 35 with two reflective surfaces 34 disposed in parallel planes at an angle of forty-five degrees from the window 30. The reflecting surfaces 34 serve to reflect the image of the diopter value on a path from the window 30 that travels to the first reflective surface, reflected ninety degrees therefrom to the second reflective surface, and reflected ninety degrees therefrom to a prism viewing window 36 visible from the front of the adaptor 42.

When the invention is in operation, the physician examines a patient by placing the ophthalmoscope 12 up to the patient's eye. The physician looks through the system eyepiece 44 and thereby views the target area. The physician manipulates the scalloped rim 20 of the lens disc 19 to achieve the desired optical parameters for the specific target area and to adjust for any refractive errors. The video adaptor 42 provides the physician and the patient with the ability to view the target area on the video monitor 62. The physician may read the diopter value by looking at the prism viewing window 36.

While the present invention has been particularly shown and described with reference to the preferred mode as illustrated in the drawing, it will be understood by one skilled in the art that various changes in detail may be effected therein without departing from the spirit and scope of the invention as defined by the claims.

We claim:

1. A hand-held opto-diagnostic medical system for viewing a target area, said system comprising:

a medical instrument including a housing having an optical passage through said housing;

a light source for illuminating the target area;

a plurality of optical lenses fixed to a rotatably mounted lens selection disc, said optical lenses having varying diopters, said disc mounted within said housing and positioned to lie in a plane perpendicular to said optical passage wherein rotation of said disc sequentially disposes one of said lenses into said optical passage;

means to indicate the diopter of one of said lenses selectively disposed in said optical passage, said indicating means located in a window in the front face of said housing;

an adapter coupled to said front face of said housing;

a beam splitter mechanically and optically coupled into said adapter, an optical input originating from said optical passage of said medical instrument and extending into said beam splitter, a first optical output of said beam splitter communicated to a system eyepiece positioned in the front face of said adapter, and a second optical output of said beam splitter communicated to a video camera head positioned within said adapter; and means for reflecting an image from said window such that said image is visible from the front side of said adaptor, said means positioned on the front face of said housing of said medical instrument.

2. The medical system of claim 1 wherein said video camera head comprises a solid state imager.

3. The medical system of claim 2 further comprising video monitoring and recording means connected to an output of said solid state imager.

4. The medical system of claim 1 wherein said adapter further comprises a rod lens to optically connect said beam splitter to said optical passage.

5. The medical system of claim 1 wherein said reflecting means comprises a prism.

* * * * *